(12) United States Patent
Hansen, Jr. et al.

(10) Patent No.: US 6,277,626 B1
(45) Date of Patent: Aug. 21, 2001

(54) PROCESS FOR THE ENZYMATIC RESOLUTION OF LACTAMS

(75) Inventors: Donald W. Hansen, Jr., Skokie; Mahima Trivedi, Glenview; Rolando E. Gapud; John S. Ng, both of Chicago; Alok K. Awasthi, Skokie, all of IL (US); Ping T. Wang, Manchester, MO (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 09/250,197

(22) Filed: Feb. 16, 1999

Related U.S. Application Data
(60) Provisional application No. 60/074,830, filed on Feb. 17, 1998.

(51) Int. Cl.$^7$ .............................. C07C 1/04; C12P 17/00; C12P 17/14; C12P 17/10
(52) U.S. Cl. ....................... 435/280; 435/117; 435/120; 435/121
(58) Field of Search ................................ 435/280, 117, 435/120, 121

(56) References Cited

U.S. PATENT DOCUMENTS

| | | |
|---|---|---|
| 5,106,750 | 4/1992 | Wong et al. . |
| 5,407,828 | 4/1995 | Kierkels et al. . |
| 5,420,037 | 5/1995 | Howell et al. . |
| 5,447,865 | 9/1995 | Wong et al. . |
| 5,492,830 | 2/1996 | Kalwass et al. . |
| 5,516,676 | 5/1996 | Hanson et al. . |
| 5,523,233 * | 6/1996 | Chartrain et al. .................... 435/280 |
| 5,529,929 | 6/1996 | Rossi, Jr. et al. . |
| 5,585,252 | 12/1996 | Wong et al. . |
| 5,620,876 | 4/1997 | Davis et al. . |

FOREIGN PATENT DOCUMENTS

| | | |
|---|---|---|
| 0115860 | 2/1984 | (EP) . |
| 0634492 | 12/1994 | (EP) . |
| 57-198098 | 12/1982 | (JP) . |
| 06 192221 * | 12/1992 | (JP) . |
| 11 113594 * | 10/1997 | (JP) . |
| WO91/00362 | 1/1991 | (WO) . |
| WO94/03428 | 2/1994 | (WO) . |
| 98/29561 * | 7/1998 | (WO) . |

OTHER PUBLICATIONS

Bryan et al., Proteases of enhanced stability: characterization of a thermostable variant of subtilisin, Proteins: Struct., Funct., Genet. 1 (4) : 326–34 (1986).*

Basak et al, "Differential Effects of Stereochemistry and C–4 Substitutents on the Enantioselectivity of PLE and PPL Catalysed Hydrolysis of 3,4–Disubstituted beta lactams", Tetrahedron Letters, 38 (4) : 643–646 (1997).*

Dugas, "The stereospecificty of subtilisin BPN' towards 1–keto–3–carbomethoxy–1,2,3,4–tetrahydroisoquinoline", Can. J. Biochem. 47 : 985–7 (1969).*

Roberge, C. et al., "Process development for the production of the (S)–acid precursor of a novel elastase inhibitor . . . " Chemical Abstracts, vol. 126(1997), No. 17, p. 239.

Babiak, K et al., Lipase–Catalyzed Irreversible Transesterification Using Enol Esters: J. Organic Chemistry (1990), vol. 55, 3377–3381.

* cited by examiner

*Primary Examiner*—Sandra E. Saucier
(74) *Attorney, Agent, or Firm*—Alan Scrivner

(57) ABSTRACT

A method of separating enantiomeric lactam esters. The lactam esters are contacted with a biocatalyst, such as an enzyme or a microorganism, in a solution wherein only one enantiomer is selectively hydrolyzed to give the optically active isomer of the corresponding acid. The hydrolysis product is then separated from the unreacted lactam esters. The enzyme is then recycled for reuse in the next enzymatic resolution. The undesired isomer is also racemized and reused in the next enzymatic resolution.

11 Claims, No Drawings

PROCESS FOR THE ENZYMATIC RESOLUTION OF LACTAMS

This application claims priority to U.S. Provisional Application No. 60/074,830 filed Feb. 17, 1998.

BACKGROUND OF THE INVENTION

1. Field of the Invention

The present invention relates to the enzymatic resolution of lactams. The method of the present invention is useful in preparing compounds which may have utility as pharmaceutical, agricultural and veterinary products or starting materials and intermediates for their synthesis.

2. Discussion of the Prior Art

It is known in the art that chiral resolution of compounds can be achieved by using enzymes. Chiral resolution using enzymes such as esterases on aliphatic esters and cyclic compounds containing esters are described in, for example, W. Boland et al., *Synthesis*, 1049–1072, 1991. Chiral resolutions using enzymes in aliphatic methyl esters hydrolysis is described in, for example, H. Ohta et al., *Chem. Lett.*, 657–660, 1992. Chiral resolutions using enzymes in cyclohexanes systems are described in, inter alia, M. Ohno, *Tet. Lett.*, 29, 6961–6964, 1988; H. Hemmerle, *Tet Lett.*, 28, 3471–3474, 1987; and B. Brion, *Tet Lett.*, 33, 4889–4892, 1992. Chiral resolutions using lipases or Acetylcholine esterases on cycloheptanes containing diacetates is found in A. J. Pearson et al., *JOC*, 54, 3882, 1989. Beta-lactams have been reported to be selectively acylated by lipase at the nitrogen function (C. Sih et al., *JOC*, 58, 1068, 1993).

However, there is no prior art for the enzymatic resolution of lactam esters. It is often desired to obtain a single enantiomer of a racemic lactam ester. These compounds can be used as intermediates for preparing compounds which have utility as starting materials and intermediates for the synthesis of pharmaceutical, agricultural and veterinary products. For example, the enanantiomerically pure form of 7-carbomethoxycaprolactam is a useful intermediate in the synthesis of pharmaceutical drug candidates.

SUMMARY OF THE INVENTION

The present invention is directed to a method of separating enantiomeric lactam esters. The lactam esters are contacted with a biocatalyst, such as an enzyme or a microorganism, in an aqueous solution, an organic solvent, or a mixture of organic and aqueous solvents, wherein only one enantiomer is selectively hydrolyzed to give the optically active isomer of the corresponding acid. The hydrolysis product is then separated from the unreacted lactam esters using standard methods known to those skilled in the art. This invention also discloses a novel method for the recycling and reuse of the enzymes as well as the racemization of either enantiomer of the lactam ester after enzymatic resolution.

DETAILED DESCRIPTION OF THE PREFERRED EMBODIMENTS

The present invention is directed to contacting racemic esters of lactam with a biocatalyst, such as an enzyme or a microorganism, whereby one of the optical isomers is selectively hydrolyzed to give the optically active isomer of the corresponding acid. The optically active products are then isolated/purified using suitable procedures.

For illustrative purposes only, the process of the present invention is demonstrated by the following example of enzymatic cleavage of a racemic 7-carbomethoxy caprolactam wherein the S configuration is converted to its acid:

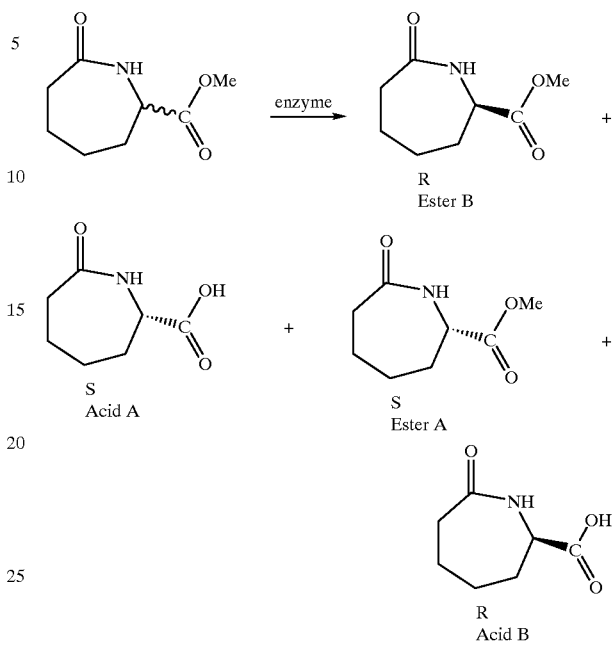

For convenience, the procedure is described herein using racemic esters of lactam; however, the method of the present invention is not limited to use with the racemic form. The lactam ester may be present in the optical active form or in nonracemic mixtures which have an excess of one of the optical isomers. The method of the present invention allows the lactam mixture to react such that only one of two enantiomeric esters of the lactam is converted to its acid.

The term "stereoselective hydrolysis" refers to the preferential hydrolysis of one enantiomer relative to another. The term "mixture" as used herein in relation to enantiomeric compounds, denotes mixtures having equal (racemic) or nonequal amounts of enantiomers. The term "resolution" denotes partial, as well as, preferably, complete resolution. The term "enzymatic process" or "enzymatic method" or "enzymatic reaction" denote a process or method or reaction of the present invention employing an enzyme or microorganism. The term "enantiomeric excess(es)" is related to the older term "optical purity". In a mixture of a pure enantiomer (R or S) and a racemate, enantiomeric excess is the percent excess of the enantiomer over the racemate. It can be expressed in the following equation, for example:

$$\text{Optical purity} = \text{percent enantiomeric excess}$$
$$= \frac{[R]-[S]}{[R]+[S]} \times 100 = \%R - \%S$$

The enzyme may be any enzyme obtainable from animals, plants, microorganisms, etc. The enzyme may be employed in any conventional form such as in a purified form, a crude form, a mixture with other enzymes, a microbial fermentation broth, a fermentation broth, a microbial body, a filtrate of fermentation broth, and the like, either solely or in combination. In addition, the enzyme or microbial body may be immobilized on a resin.

The activities of the enzymes used in this invention are expressed in "units". Units are defined as the rate of hydrolysis of p-nitrophenyl proprionate per minutes as expressed in μmol/min at room temperature.

Specific examples of the enzyme are those obtained from animal and plants such as cow liver esterase, pig liver esterase, pig pancreas esterase, horse liver esterase, dog liver esterase, pig phosphatase, amylase obtainable from barley and potato and lipase obtainable from wheat. Other examples are hydrolases obtained from such microorganisms as Rhodotorula, Trichoderma, Candida, Hansenula, Pseudomonas, Bacillus, Achromobacter, Nocardia, Chromobacterium, Flavobacterium, Rhizopus, Mucor, Aspergillus, Alkaligenes, Pediococcus, Klebsiella, Geotrichum, Lactobaccilus, Cryptococcus, Pichia, Aureobasidium, Actinomucor, Enterobacter, Torulopsis, Corynebacterium, Endomyces, Saccaromyces, Arthrobacter, Metshnikowla, Pleurotus, Streptomyces, Proteus, Gliocladium, Acetobacter, Helminthosporium, Brevibacterium, Escherichia, Citrobacter, Absidia, Micrococcus, Microbacterium, Penicillium and Schizophyllium as well as from lichen and algae.

Specific examples of the microorganisms useful in the present invention include, but are not limited to, *Rhodotorula minuta, Rhodotorula rubra, Candida krusei, Candida cylindracea, Candida tropicalis, Candida utilus, Pseudomonas fragi, Pseudomonas putida, Pseudomonas fluorescens, Pseudomonas aeruginosa, Rhizopus chinensis, Mucor pusillus, Aspergillus niger, Alkaligenes faecalis, Torulopsis ernobii, Bacillus cereus, Bacillus subtilis, Bacillus pulmilus, Bacillus subtilis* var. *niger, Citrobacter freundii, Micrococcus varians, Micrococcus luteus, Pediococcus acidlactici, Klebsiella pneumoriae, Absidia hyalospora, Geotrichun candidum, Schizophyllum commune, Nocardia uniformis subtsuyanarenus, Nocardia uniformis, Chromobacterium chocolatum, Hansenula anomala* var. *ciferrii, Hansenula anomala, Hansenula polymorpha, Achromobacter lyticus, Achromobacter parvulus, Achromobacter simplex, Torulopsis candida, Corynebacterium sepedonicum, Endomyces geotrichum, Saccaromyces carrvisial, Arthrobacter globiformis, Streptomyces grisens, Micrococcus luteus, Enterobacter cloacae, Corynebacterium ezui, Lacto bacillus casei, Cryptococcus albidus, Pichia polimorpha, Penicillium frezuentans, Aureobasidium pullulans, Actinomucor elegans, Streptomyces grisens, Proteus vulgaris, Gliocladium roseum, Gliocladium virens, Acetobacter aurantius, Helminthosporium* sp. *Chromobacterium iodinum, Chromobacterium violaceum, Flavobacterium lutescens, Metschnikowia pulcherrima, Pleurotus ostreatus, Brevibacterium ammoniagenes, Brevibacterium divaricatum, Escherichia coli, Rodotolura minuta* var. *texensis, Trichoderma longibrachiatum, Mucor javanicus, Flavobacterium arbonescens, Flavobacterium heparinum,* and *Flavobacterium capsulatum.*

Exemplary, commercially available enzymes suitable for use in the present invention include lipases such as Amano PS-30 (*Pseudomonas cepacla*), Amano GC-20 (*Geotrichum candidum*), Amano APF (*Aspergillus niger*), Amano AK (Pseudomonas sp.), Pseudomonas fluorescens lipase (Biocatalyst Ltd.), Amano Lipase P30 (Pseudomonas sp.), Amano P (*Pseudomonas fluorescens*), Amano AY-30 (*Candida cylindracea*), Amano N (*Rhizopus niveus*), Amano R (Penicillium sp.), Amano FAP (*Rhizopus oryzae*), Amano AP-12 (*Aspergillus niger*), Amano MAP (*Mucor melhei*), Amano GC-4 (*Geotrichum candidum*), Sigma L-0382 and L-3126 (porcine pancrease), Lipase OF (Sepracor), Esterase 30,000 (Gist-Brocarde), KID Lipase (Gist-Brocarde), Lipase R (Rhizopus sp., Amano), Sigma L-3001 (Wheat germ), Sigma L-1754 (*Candida cytindracea*), Sigma L-0763 (*Chromobacterlum vlscosum*) and Amano K-30 (*Aspergillus niger*). Additionally, exemplary enzymes derived from animal tissue include esterase from pig liver, chymotrypsin and pancreatin from pancreas such as Porcine Pancreatic Lipase (Sigma). Two or more, as well as a single, enzyme may be employed when carrying out the process of the present invention.

In addition, enzymes which are serine carboxypeptidases can be used. These enzymes are derived from *Candida lipolytica, Saccharomyces cerevisiae,* wheat (*Triticum aestivum*) and *Penicillium janthinellum.* Commercially available cross-linked enzyme crystals may also be used such as from Altus Biologics, Inc.(e.g. ChiroCLEC-CR, ChiroCLEC-PC, ChiroCLEC-EC).

The present invention is also directed to the use of thermostable esterases and genetically engineered esterases for the resolution of the lactam esters. These enzymes, commercially available from ThermoGen, Inc., are especially suitable for use in industrial processes and are easy to use. In addition to functioning at a wide range of temperatures including higher temperatures, these thermostable enzymes possess an increased shelf life which improves handling. The enzymes are also able to endure harsh, non-biological conditions (pH, salt concentrations, etc.) usually associated with industrial processes because of their stability under operational conditions. They can be immobilized for reuse in multiple applications and hence improving the cost-effectiveness of the process.

During the isolation of the products after enzymatic resolution, the enzymes are frequently exposed to traces of organic solvents. In addition, some enzymatic resolutions are found to work best under a mixture of aqueous and organic solvents or in organic solvents alone. The esterase enzymes of the present invention are more tolerant to denaturing by many organic solvents compared to conventional enzymes which allows longer operational half lives. Most of the esterase enzymes are produced using genetic engineering techniques of gene cloning which ensures the purity of these enzymes and the ease of process controls during scale up.

It was discovered that many esterase and lipase enzymes offer a high degree of stereoselectivity in the resolution of the lactam esters. The preferred enzymes for the resolutions of lactam esters include the thermoesterases THERMOCAT E002, THERMOCAT E010, THERMOCAT E015, THERMOCAT E020 from ThermoGen, Inc. with the most preferred enzymes being the THERMOCAT E020.

Instead of isolated enzymes, there may also be employed a microorganism which can produce any enzyme as stated above.

The enzyme or microorganisms may be used alone or in combination. Depending upon the type of enzyme or microorganism used, either one of the optical isomers of the lactam ester is predominantly hydrolyzed to give the optically active acid. Either one of the optical isomers may be obtained by the selection of a suitable enzyme or microorganism.

The enzymatic hydrolysis of the present invention may be carried out by contacting the lactam esters with the enzyme or microorganism, usually in an aqueous buffer medium with good agitation.

The buffer medium may be inorganic acid salt buffers (e.g. potassium dihydrogen phosphate, sodium dihydrogen phosphate), organic acid salt buffers (e.g. sodium citrate), or any other suitable buffer. The concentration of the buffer may vary from 0.005 to 2 M, preferably from 0.005 to 0.5

M and will depend on the specific lactam ester and the enzymes microorganism used.

Depending on the solubility of the lactam esters, a surfactant may be added to the reaction mixture to solubilize the substrate; preferred surfactants include but are not limited to nonionic surfactants such as alkylaryl polyether alcohols. A preferred surfactant is octylphenoxy polyethoxyethanol, commercially available as Triton X-100 (from Sigma Chemical Company). An effective amount of a surfactant is used. Typical amounts can vary from 0.05% to about 10%.

It is sometimes preferable to add an effective amount of an organic cosolvent to increase product solubility to facilitate the reaction. Examples of solvents include but are not limited to acetonitrile, THF, DMSO, DMF, alcohols, etc. Effective amounts of a co-solvent includes from 1% to 30% depending on the specific lactam ester and the enzymes microorganism used.

The pH of the buffers or the pH of the reaction is normally from 4 to 10, preferably from 5 to 9, most preferably from 7 to 8. The reaction temperature may vary from 0 to 100° C. and will depend on the specific lactam ester and the enzymes or microorganism used. The reaction time is generally from 1 hour to 70 hours and will depend on and/or specific lactam ester, enzyme concentration and the enzymes the microorganism used. Normally, the enzymatic hydrolysis is allowed to proceed for a period sufficient to generate a satisfactory quantity of the desired esters or acid in satisfactory optical purity. As the reaction progresses, the amount of desired ester or acid and their optical purities may be monitored by HPLC and chiral HPLC. Normally, the conversion is carried to approximately 50%, after which the acid and the esters are usually obtained in good yields after isolation.

The amount of enzyme used could vary widely from 5 units to 12,000 units of enzyme per mole of starting materials. (The activities of the enzymes used in this invention are expressed in "units". Units are defined as the rate of hydrolysis of p-nitrophenyl proprionate per minutes as expressed in $\mu$mol/min at room temperature). The amount of enzyme needed will depend on the temperature, the specific lactam ester, the enzymes and/or microorganism used, and the desirable reaction time. It may also be desirable to use a large amount of enzymes in some cases to ensure a practically short reaction time, especially when the enzymes are immobilized and can be reused for many turnovers. The concentration of the ester substrate may be from 0.1 g/L to 100 g/L and depends on the specific lactam ester and the enzyme and/or microorganism used.

The enzymes and/or microorganisms used in the present invention may be in crude form or in an immobilized form. They can be immobilized on various solid supports without loss of stereospecificity or change in stereo selectivity. The solid supports can be inert absorbents to which the enzyme is not covalently bonded. Instead the enzyme is absorbed such as by interactions of hydrophobic or hydrophilic portions of a protein with like regions of the inert absorbent, by hydrogen bonding, by salt bridge formation, or by electrostatic interactions. Inert absorbent materials include, but are not limited to, synthetic polymers (e.g. polystyrene, poly-(vinylalcohol), polyethylene and polyamides), mineralaceous compounds (e.g. diatomaceous earth and Fuller's earth), or naturally occurring polymers (e.g. cellulose). Specific examples of such materials include Celite 545 diatomaceous earth, Abelite XAD-8 polymeric resin beads and polyethylene glycol 8000.

The enzyme may also be immobilized on the support to which the enzyme is covalently bonded (e.g., oxirane-acrylic beads and glutaraldehyde activated supports). Specific examples include Eupergit C oxirane-acrylic beads and glutaraldehyde activated Celite 545. Other possible immobilizing systems are well known and are readily available to those skilled in the art of enzyme immobilization.

Instead of conventional immobilization method described above, it was discovered that the enzymes could also be conveniently recycled for reuse by simply precipitating out the used enzymes with ammonium sulfate. The precipitated enzyme-ammonium sulfate could be used directly in the next enzymatic hydrolysis. Salts are commonly used in purification of enzymes. They generally protect the protein enzymes by reducing solvent activity. It was discovered that ammonium sulfate, potassium sulfate, potassium phosphate, sodium chloride etc. are effective in recovering the enzyme thermoesterase (E020) activity. Among the salts, ammonium sulfate is the most preferred one.

The desired products, the optically pure (or enriched) unreacted ester and the optically pure (or enriched) acid may be isolated from the hydrolysis mixture using conventional methods such as extractions, acid-base extractions, filtration, chromatography, crystallization or combinations thereof. The recovered enzyme or microorganism may be recycled as described above.

In a convenient isolation procedure, after the enzymatic hydrolysis, the pH is adjusted to pH 7.5 to 8 (in the case of immobilized biocatalysts, the biocatalyst is first separated by filtration), the product acid is separated from the unreacted ester by extracting the ester with an organic solvent such as methylene chloride, ethyl acetate, diethyl ether, methyl t-butyl ether, or any other solvent in which the substrate is soluble and stable. Concentration of the organic extracts affords the optically pure (or enriched) unreacted ester. Concentration of the aqueous phase yield the optically pure (or enriched) acid.

The acid can be freed of the buffer salts and enzyme by selective precipitation or chromatography or other methods known to those skilled in the art. These include acidifying the aqueous to pH 3 (or lower) and isolating the acid by extracting the acid with organic solvent such as methylene chloride, ethyl acetate, diethyl ether, methyl t-butyl ether, or any other solvent in which the acid is soluble and stable. Concentration of the organic extracts affords the optically pure (or enriched) unreacted ester and the optically pure (or enriched) acid and which can be purified and freed of the buffer salts and enzyme by selective precipitation or chromatography or other methods known to those skilled in the art.

Either of the optically pure (or enriched) unreacted ester and the optically pure (or enriched) acid could be racemized if so desired. The optically pure (or enriched) unreacted ester could be racemized by heating in the appropriate base under appropriate conditions. Alternatively, the optically pure (or enriched) unreacted ester could be racemized by heating in acid in the presence of an alcohol under appropriate conditions. The optically pure (or enriched) unreacted acid could also be racemized and converted to the racemic esters by heating in acid in the presence of an alcohol under appropriate conditions. In this manner, excellent yields can be achieved of either the optically pure (or enriched) unreacted ester or the optically pure (or enriched) acid by this combination of stereoselective enzymatic hydrolysis and racemization techniques.

In a preferred embodiment, the present invention is directed to the enzymatic

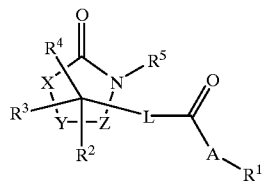

(I)

resolution of lactams of the formula (I):

(I)

$R^1$ is selected from the group consisting of alkyl, alkenyl, alkynyl, cycloalkyl, cycloalkenyl, heterocyclyl, aryl, and heteroaryl which may optionally be substituted by one or more of the following alkyl, alkenyl, alkynyl, hydroxy, alkoxy, thiol, thioalkoxy, halogen, nitro, amino, alkylamino, dialkylamino, aminoalkyl, dialkylaminoalkyl, arylamino, aminoaryl, alkylaminoaryl, cyano, haloalkyl;

A is selected from the group consisting of O, S, and NH or N which may be substituted respectively with one or two independent $R^1$ (the $R^1$s need not be the same);

L is selected from the group consisting of no group or alkylene, alkenylene, alkynylene, and —$(CH_2)_m$—D—$(CH_2)_n$—;

D is selected from the group consisting of O, S, SO, $SO_2$, Se, SeO, $SeO_2$, N—$R^6$;

$R^6$ is selected from the group consisting of hydrogen, alkyl, alkenyl, alkynyl, cycloalkyl, cycloalkenyl, heterocyclyl, aryl, and heteroaryl which may optionally be substituted by one or more of the following: alkyl, alkenyl, alkynyl, hydroxy, alkoxy, thiol, thioalkoxy, halogen, nitro, amino, alkylamino, dialkylamino, aminoalkyl, dialkylaminoalkyl, arylamino, aminoaryl, alkylaminoaryl, cyano, haloalkyl;

m=0 to about 7;

n=1 to about 5;

wherein L may optionally be substituted by one or more of the following: alkyl, alkenyl, alkynyl, hydroxy, alkoxy, thiol, thioalkoxy, $S(O)R^7$, $S(O)_2R^7$, halogen, nitro, amino, alkylamino, dialkylamino, aminoalkyl, dialkylaminoalkyl, arylamino, aminoaryl, alkylaminoaryl, cyano, haloalkyl, wherein all said substitutions may be optionally substituted with one or more of the following: alkyl, amino, alkylamino, dialkylamino, aminoalkyl, and $R^7$ is alkyl, or aryl;

X is selected from the group consisting of NH, O, S, Se, $(CH_2)_p$, and CH=CH;

p=0 to about 4;

Y is selected from the group consisting of NH, O, S, SO, $SO_2$, Se, SeO, $SeO_2$, $(CH2)_q$, CH=CH;

q=0 to about 2;

Z is selected from the group consisting of $(CH_2)_v$, CH=CH;

v=0 to about 2;

$R^2$, $R^3$, and $R^4$ are independently selected from alkyl, alkenyl, alkynyl, hydroxy, alkoxy, thiol, thioalkoxy, $S(O)R^7$, $S(O)_2R^7$, halogen, nitro, amino, alkylamino, dialkylamino, aminoalkyl, dialkylaminoalkyl, arylamino, aminoaryl, alkylaminoaryl, cyano, haloalkyl, wherein all said substitutions may be optionally substituted with one or more of the following: halogen, alkyl, amino, alkylamino, dialkylamino, aminoalkyl, hydroxy, alkoxy, and $R^5$ is independently selected from hydrogen, alkyl, alkenyl, alkynyl, hydroxy, alkoxy, thiol, thioalkoxy, $S(O)R^7$, $S(O)_2R^7$, halogen, nitro, amino, alkylamino, dialkylamino, aminoalkyl, dialkylaminoalkyl, arylamino, aminoaryl, alkylaminoaryl, cyano, haloalkyl, wherein all said substitutions may be optionally substituted with one or more of the following: halogen, alkyl, amino, alkylamino, dialkylamino, aminoalkyl, hydroxy, alkoxy;

$R^2$, $R^3$, may optionally be taken together to form an alicyclic hydrocarbon, heterocyclyl, heteroaryl or aromatic hydrocarbon and said optionally formed ring may be optionally substituted with one or more of alkyl, alkenyl, alkynyl, hydroxy, alkoxy, thiol, thioalkoxy, $S(O)R^7$, $S(O)_2R^7$, halogen, nitro, amino, alkylamino, dialkylamino, aminoalkyl, dialkylaminoalkyl, arylamino, aminoaryl, alkylaminoaryl, cyano, or haloalkyl.

Preferably, the present invention is directed to the enzymatic resolution of lactams

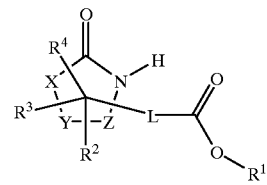

(II)

of the formula (II):

(II)

$R^1$ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

L is selected from the group consisting of no group or alkylene, alkenylene, and alkynylene;

wherein L may optionally be substituted by one or more of the following: alkyl, alkenyl, alkynyl, hydroxy, alkoxy, thiol, thioalkoxy, halogen, nitro, amino, alkylamino, dialkylamino, aminoalkyl, dialkylaminoalkyl, arylamino, aminoaryl, alkylaminoaryl, cyano, and haloalkyl;

X is selected from the group consisting of $(CH_2)_p$, and CH=CH;

p=0 to about 4;

Y is selected from the group consisting of NH, O, $(CH_2)_q$ and CH=CH;

q=0 to about 2;

Z is selected from the group consisting of $(CH_2)_v$ and CH=CH;

v=0 to about 2;

$R^2$, $R^3$, and $R^4$ are independently selected from alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy;

More preferably the present invention is directed to the enzymatic resolution of

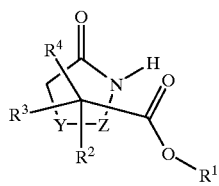

(III)

lactams of the formula (III):

(III)

$R^1$ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

Y is selected from the group consisting of NH, O, $(CH_2)_q$ and CH=CH;

q=0 to about 2;

Z is selected from the group consisting of $(CH_2)_v$ and CH=CH;

v=0 to about 2;

$R^2$, $R^3$, and $R^4$ are independently selected from alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

Even more preferably, the present invention is directed to the enzymatic resolution of lactams of the formula (IV):

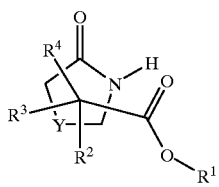

(IV)

$R^1$ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

Y is selected from the group consisting of NH, O, $(CH_2)_q$ and CH=CH;

q=0 to about 2;

$R_2$, $R_3$, and $R_4$ are independently selected from alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

Most preferred the present invention is directed to the enzymatic resolution of lactams of the formula (V):

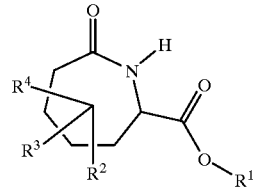

(V)

$R^1$ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

$R^2$, $R^3$, and $R^4$ are independently selected from alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

As utilized herein, the term "alkyl", alone or in combination, means an acyclic alkyl radical containing from 1 to 10, preferably from 1 to 8 carbon atoms and more preferably 1 to 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl" refers to an unsaturated acyclic hydrocarbon radical in so much as it contains at least one double bond. Such radicals containing from 2 to 10 carbon atoms, preferably from 2 to 8 carbon atoms and more preferably 2 to 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "alkynyl" refers to an unsaturated acyclic hydrocarbon radical in so much as it contains one or more triple bonds, such radicals containing 2 to 10 carbon atoms, preferably having from 2 to 8 carbon atoms and more preferably having 2 to 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclyl" means an unsaturated cyclic hydrocarbon radical with 3 to about 6 carbon atoms, wherein 1 to about 4 carbon atoms are replaced by nitrogen, oxygen or sulfur. The "heterocyclyl" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxinyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "aryl" means an aromatic hydrocarbon radical of 4 to 16 carbon atoms, preferably 6 to about 12 carbon atoms, more preferably 6 to 10 carbon atoms. Examples of suitable aromatic hydrocarbon radicals include phenyl, naphthyl, and the like.

The term "heteroaryl" means aromatic hydrocarbon radical of 4 to 16 carbon atoms, preferably 6 to about 12 carbon atoms, more preferably 6 to 10 carbon atoms wherein 1 to about 4 carbon atoms are replaced by nitrogen, oxygen or sulfur.

The terms "cycloalkyl" or "cycloalkenyl" means an "alicyclic radical in a ring with 3 to 10 carbon atoms, and preferably from 3 to 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "halogen" means fluorine, chlorine, bromine or iodine.

The term "prodrug" refers to a compound that is made more active in vivo.

As used herein, reference to "treatment" of a patient is intended to include prophylaxis.

EXAMPLES

Example 1

Enzymatic Resolution of Racemic 7-carbomethoxycaprolactam

Four enzymes were each dissolved in 20 mL of buffer (pH 7, Sigma phosphate buffer with conc. of 0.1 mol/liter) to form four separate solutions. Racemic 7-carbomethoxycaprolactam was added to each solution. Each solution was then allowed to react at room temperature (20–25 ° C.). Aliquots were drawn (non-uniform in volume) at specific time intervals and their pH measured.

Each aliquot was then acidified to pH=1 with 0.5N KHSO$_4$ and then extracted with methylene chloride. The organic layer was separated, dried (MgSO$_4$), filtered, stripped in vacuo and submitted for HPLC analysis. The mass recovery averaged 60%. The results are shown in Table 1.

TABLE 1

Chiral HPLC Assay By Area Percent at Varying Time Intervals

| Rxn Time | HPLC Area % Acid A | HPLC Area % Acid B | HPLC Area % Ester A | HPLC Area % Ester B | pH |
|---|---|---|---|---|---|
| Altus Biologics Enzyme #13 (*Candida Antarctica* B. Lipase) 25 mg of Enzyme per 500 mg Caprolactam methylester | | | | | |
| T = 15 min | 18.3 | 6.6 | 25.8 | 49.2 | 7 |
| T = 30 min | 26.2 | 12.0 | 15.8 | 45.9 | 5 |
| T = 1 H | 29.2 | 16.4 | 12.2 | 42.1 | 4 |
| T = 2 H | 31.2 | 21.0 | 8.7 | 38.7 | 3 |
| T = 4 H | 31.5 | 21.3 | 6.9 | 40.2 | 3 |
| Altus Biologics Enzyme #13 (*Candida Antarctica* B. Lipase) 50 mg of Enzyme per 500 mg Caprolactam methylester | | | | | |
| T = 15 min | 26.6 | 11.9 | 18.2 | 43.0 | 5 |

TABLE 1-continued

Chiral HPLC Assay By Area Percent at Varying Time Intervals

| Rxn Time | HPLC Area % Acid A | HPLC Area % Acid B | HPLC Area % Ester A | HPLC Area % Ester B | pH |
|---|---|---|---|---|---|
| T = 30 min | 29.9 | 15.5 | 14.6 | 39.7 | 4 |
| T = 1 H | 29.4 | 16.7 | 12.8 | 40.7 | 3–4 |
| T = 2 H | 33.7 | 20.9 | 8.6 | 36.7 | 3 |
| T = 4 H | 35.3 | 23.1 | 0.0 | 41.7 | 3 |
| Altus Biologics Enzyme #16 (Chiroclec-BL) 4 mg of Enzyme per 500 mg Caprolactam methylester | | | | | |
| T = 15 min | 11.7 | 6.7 | 35.1 | 46.4 | 7–8 |
| T = 30 min | 19.7 | 12.1 | 26.8 | 41.1 | 7–8 |
| T = 1 H | 20.7 | 13.4 | 25.3 | 40.6 | 6 |
| T = 2 H | 21.7 | 14.8 | 23.5 | 40.1 | 5 |
| T = 4 H | 22.6 | 15.8 | 22.5 | 39.2 | 4–5 |
| Altus Biologics Enzyme #16 (Chiroclec-BL) 8 mg of Enzyme per 500 mg Caprolactam methylester | | | | | |
| T = 15 min | 16.6 | 9.5 | 31.9 | 42.1 | 7–8 |
| T = 1 H | 24.5 | 15.7 | 23.0 | 36.8 | 5–6 |
| T = 1.5 H | 23.3 | 16.1 | 23.0 | 36.8 | 5 |
| T = 2 H | 23.6 | 14.6 | 23.3 | 38.5 | 4–5 |
| T = 4 H | 22.0 | 14.0 | 23.8 | 40.3 | 4–5 |

Example 2

Enzymatic Resolution of Racemic 7-carbomethoxycaprolactam

Seven enzymes were each dissolved in 50 mL of buffer (pH 7) (phosphoric acid added to Sigma phosphate buffer with conc. of 0.1 mol/liter and pH 7.4) to form seven separate solutions. Racemic 7-carbomethoxycaprolactam was added to each solution so that 500 units of enzyme were used per 500 mg of ester substrate. Each solution was then allowed to react at room temperature (20–25 ° C.). Aliquots were drawn (non-uniform in volume) at specific time intervals and their pH measured.

Each aliquot was then acidified to pH=1 with 1M KHSO$_4$ and then extracted with methylene chloride. The organic layer was separated, dried (MgSO$_4$), filtered, stripped in vacuo and submitted for HPLC analysis. The mass recovery averaged 50–60%. The results are shown in Table 2.

TABLE 2

Extraction Work Up

THERMOGEN HYDROLYSIS ENZYMES
(500 U WITH 500 mg Caprolactam methylester)

| Enzyme # | HPLC Area % Acid A | HPLC Area % Acid B | HPLC Area % Ester A | HPLC Area % Ester B |
|---|---|---|---|---|
| T = 2H | | | | |
| E001 | 0.8 | 0.0 | 28.0 | 38.9 |
| E002 | 2.2 | 0.0 | 37.3 | 59.1 |
| E006 | 1.7 | 0.0 | 40.1 | 57.7 |
| E009 | 0.0 | 0.0 | 46.8 | 51.8 |
| E010 | 9.9 | 0.5 | 30.4 | 59.3 |
| E014 | 1.7 | 0.4 | 44.6 | 53.4 |
| E015 | 6.1 | 0.3 | 35.3 | 57.8 |
| T = 4H | | | | |
| E001 | 3.5 | 0.0 | 20.7 | 52.5 |
| E002 | 11.0 | 0.6 | 21.0 | 65.8 |
| E006 | 12.8 | 0.7 | 19.3 | 66.9 |
| E009 | 1.0 | 0.0 | 44.8 | 53.3 |

TABLE 2-continued

Extraction Work Up

THERMOGEN HYDROLYSIS ENZYMES
(500 U WITH 500 mg Caprolactam methylester)

| Enzyme # | HPLC Area % Acid A | HPLC Area % Acid B | HPLC Area % Ester A | HPLC Area % Ester B |
|---|---|---|---|---|
| E010 | 14.6 | 1.1 | 14.2 | 70.1 |
| E014 | 3.0 | 0.2 | 41.5 | 55.3 |
| E015 | 2.7 | 0.3 | 8.5 | 23.8 |
| T = 9H | | | | |
| E001 | 37.4 | 4.9 | 2.6 | 53.2 |
| E002 | 35.7 | 4.6 | 3.0 | 55.8 |
| E006 | 12.2 | 1.8 | 0.8 | 17.4 |
| E009 | 9.6 | 1.6 | 34.9 | 46.6 |
| E010 | 23.1 | 3.0 | 1.9 | 72.1 |
| E014 | 5.1 | 3.2 | 36.8 | 54.9 |
| E015 | 18.9 | 5.4 | 8.9 | 66.9 |
| T = 20H | | | | |
| E001 | 33.3 | 8.4 | 0.5 | 57.0 |
| E002 | 32.5 | 6.7 | 0.3 | 55.6 |
| E006 | 24.9 | 4.6 | 1.2 | 59.0 |
| E009 | 6.1 | 0.7 | 31.9 | 58.0 |
| E010 | 21.9 | 3.1 | 0.0 | 75.0 |
| E014 | 4.4 | 0.6 | 31.4 | 63.6 |
| E015 | 14.2 | 1.3 | 4.1 | 80.4 |

Four of the enzymes were also separately worked up with 1M KHSO$_4$ and then lyophilized. The residue was extracted extensively with methylene chloride. The extracts were stripped in vacuo and submitted for HPLC analysis. This method improved mass recovery to about 90%. The results are shown in Table 3. As can be seen in Table 3, the pH drops steadily during the hydrolysis reaction.

TABLE 3

Lyophilization Work Up

| Rxn Time | HPLC Area % Acid A | HPLC Area % Acid B | HPLC Area % Ester A | HPLC Area % Ester B | mg cov-ered | pH |
|---|---|---|---|---|---|---|
| THERMOGEN HYDROLYSIS ENZYME E002 (500 U with 500 mg Caprolactam methylester) | | | | | | |
| T = 2H | 21.6 | 1.8 | 28.7 | 47.9 | 75.0 | 6.8 |
| T = 4H | 35.2 | 2.2 | 14.0 | 48.7 | 80.0 | 6.2 |
| T = 8H | 51.4 | 4.1 | 2.5 | 42.0 | 305.0 | 6.2 |
| THERMOGEN HYDROLYSIS ENZYME E010 (500 U with 500 mg Caprolactam methylester) | | | | | | |
| T = 2H | 19.9 | 2.7 | 30.2 | 46.1 | 85.0 | 6.8 |
| T = 4H | 33.0 | 3.1 | 15.1 | 47.7 | 79.0 | 6.6 |
| T = 8H | 42.3 | 3.5 | 3.5 | 49.6 | 301.0 | 6.5 |
| THERMOGEN HYDROLYSIS ENZYME E015 (500 U with 500 mg Caprolactam methylester) | | | | | | |
| T = 2H | 15.8 | 1.1 | 36.1 | 45.9 | 91.0 | 6.8 |
| T = 4H | 27.8 | 1.4 | 20.8 | 48.7 | 82.0 | 6.3 |
| T = 8H | 37.8 | 1.6 | 11.3 | 48.7 | 260.0 | 6.4 |
| THERMOGEN HYDROLYSIS ENZYME E020 (500 U with 500 mg Caprolactam methylester) | | | | | | |
| T = 2H | 16.0 | 2.7 | 32.6 | 48.5 | 98.0 | 6.8 |
| T = 4H | 32.3 | 3.4 | 13.6 | 50.7 | 80.0 | 6.5 |
| T = 8H | 45.4 | 6.6 | 1.1 | 46.3 | 305.0 | 6.4 |

Example 3

Enzymatic Resolution of Racemic 7-carbomethoxycaprolactam

A reaction was conducted using E002 under the conditions set forth in Example 2 except that a pH stat was employed to maintain a constant pH of 7 throughout the reaction. The enzyme was worked up with 1M KHSO$_4$ and then lyophilized. The residue was extracted extensively with methylene chloride. The extract was stripped in vacuo and submitted for HPLC analysis. The results are shown in Table 4.

TABLE 4

Lyophilization Work Up

THERMOGEN HYDROLYSIS ENZYME E020
(500 U with 500 mg Caprolactam methylester)

| Rxn Time | HPLC Area % Acid A | HPLC Area % Acid B | HPLC Area % Ester A | HPLC Area % Ester B |
|---|---|---|---|---|
| T = 2H | 15.8 | 1.0 | 33.4 | 47.0 |
| T = 4H | 28.7 | 1.7 | 19.5 | 50.1 |
| T = 6H | 42.0 | 3.1 | 8.2 | 46.7 |
| T = 8H | 45.3 | 5.2 | 3.8 | 45.0 |

The reaction was kept at pH 7 using a pH stat.
Solvents used were pH 7 phosphate buffer, and 0.1 N NaOH.

Example 4

Enzymatic Resolution of Racemic 7-carbomethoxycaprolactam at Temperatures Above Room Temperatures A solution of 33.3 g sodium hydrogenphosphate in 2000 mL DI(deionized) water was charged to a reaction vessel followed by a solution of 22.4 g potassium dihydrogenphosphate in 1300 mL DI water. The reaction mixture was stirred for 15 minutes at 47° C.–48° C. and 2.28 g ThermoCat E020 biocatalyst (activity: 18.5 units/mg) was added. The reaction mixture was stirred for 5 min or until a homogeneous solution was obtained. To the above mixture is added 60 g of 7-carbomethoxy caprolactam and the reaction mixture was stirred at 47° C.–48° C. The progress of the reaction has monitored by HPLC. When undesired ester enantiomer is completely disappeared, which takes 3 to 8 h, the temperature of reaction mixture was brought down to 25° C.–27° C. The product mixture is extracted with 3×1100 mL dichloromethane. The organic layer was dried over anhydrous magnesium sulfate, filtered over celite and concentrated to dryness below 25° C. to give 22 g of a white waxy solid (73% of theory). HPLC analysis and comparison with standard samples indicated the solid isolated is the desired desired R-enantiomer.

Example 5

Procedures for the Recycling and Re-use of Enzymes Enzyme Precipitation

A 20-ml reaction mixture containing 2 mmoles of phosphate buffer (pH 7.6), 140 units of the thermoesterase ThermoCat E020 and 200 mg of the substrate, 7-carbomethoxy caprolactam, was incubated at 48° C. in a water bath shaker for 2 hours. A control was run in parallel without the addition of enzyme preparation. At the end of reaction, a 18 ml aliquot was collected and gently mixed with 7.2 g of ammonium sulfate. After the salt was completely dissolved, the solution reaches approximately 60% saturation and the protein enzyme was precipitated. The protein enzyme was then recovered by centrifugation at 4° C. for 20 minutes.

Recycling and Re-use of Enzyme

The precipitated protein enzyme was re-dissolved in 1.8 mmoles phosphate buffer (pH 7.6) and tested in a second batch reaction of an 18 ml re-constituted mixture. The substrate 7-carbomethoxy caprolactam was reduced to 180 mg and the reaction was followed by the same procedure as described above. At end of the second reaction, a 16 ml aliquot was collected and 6.4 g ammonium sulfate were used to isolate the enzyme. The third recycle reaction was conducted in a16 ml re-constituted mixture containing 160 mg substrate by the same procedure. The products are analyzed by HPLC analyses. The results (HPLC area percentages) of these experimental are shown in the Table 5:

TABLE 5

| Samples | Time | HPLC Area % by Species | | | HPLC Area % Total | | | ee |
|---|---|---|---|---|---|---|---|---|
| | | acid | ester A | ester B | acid | ester A | ester B | |
| Reaction mixture | 0 min. | 0 | 50 | 50 | 0 | 50 | 50 | 0% |
| The first reaction | | | | | | | | |
| Control | 120 min | 17 | 41 | 41 | 100 | 50 | 50 | 0% |
| Reaction mixture | 120 min | 59 | 8 | 34 | 100 | 18 | 82 | 63.6% |
| The second reaction (first recycle) | | | | | | | | |
| Control | 120 min | 40 | 30 | 30 | 100 | 51 | 49 | 0% |
| Reaction mixture | 120 min | 53 | 5 | 42 | 100 | 11 | 89 | 77.2% |
| The third reaction (second recycle) | | | | | | | | |
| Control | 120 min | 42 | 32 | 26 | 100 | 56 | 44 | 0% |
| Reaction mixture | 120 min | 43 | 15 | 44 | 100 | 25 | 75 | 49.3% |

From the above data, it can be concluded this enzyme recycling procedures with ammonium sulfate precipitation is a simple method to recyle the enzyme for re-use.

Example 6

Procedures for the Racemization of Chiral 7-carbomethoxy Caprolactam

Method A

To a mixture of 5 microliters of 25% sodium methoxide in methanol (22 micromoles of sodium methoxide) and 1 mL of dry tetrahydrofuran (THF) under nitrogen was added 54 mg of optically pure (R)-7-carbomethoxy caprolactam. The mixture was stirred at room temperatures for 48 hours. The product was filtered through Dowex® 50WX200 ion-exchange resin (Dowex-50W-hydrogen, strongly acidic, prewashed with water but not dried), washed with additional THF and evaporated to dryness to give 44 mg of product. HPLC analysis of the product indicated that the starting material, (R)-7-carbomethoxy caprolactam, was completely racemized to a 50/50 mixture of the R and S isomers, (R)-7-carbomethoxy caprolactam and (S)-7-carbomethoxy caprolactam.

It is understood to those skilled in the art that if one would start with the (S)-7-carbomethoxy caprolactam as the starting material, the same racemic product mixture would result.

Method B

To a mixture of 1 mL of dry tetrahydrofuran (THF) and 54 mg of optically pure (R)-7-carbomethoxy caprolactam under nitrogen was added 0.47 mL of lithium diisopropylamide (LDA)/THF in cyclohexane (1.5M, 70 millimoles of LDA). The mixture was stirred at room temperatures for 1 hour. The product was filtered through Dowex® 50WX200 ion-exchange resin (Dowex-50W-hydrogen, strongly acidic, prewashed with water but not dried), washed with additional THF and evaporated to dryness to give 34 mg of product. HPLC analysis of the product indicated that the starting material, (R)-7-carbomethoxy caprolactam, has completely racemized to a 50/50 mixture of the R and S isomers, (R)-7-carbomethoxy caprolactam and (S)-7-carbomethoxy caprolactam, along with some racemized carboxylic acid.

It is understood to those skilled in the art that if one would start with the (S)-7-carbomethoxy caprolactam as the starting material, the same racemic product mixture would result.

Method C

To 20 mL of 25% sodium methoxide in methanol was added 64 mg of optically pure (R)-7-carbomethoxy caprolactam. The mixture was stirred to reflux for 24 hours. The product was cooled to 0° C., the product was acidified, extracted with methylene chloride. The organic layer was concentrated to give 5 mg of solid. The aqueous layer was concentrated to dryness, the residue solid was extracted with THF, filtered and concentrated to dryness to give 24 mg of brown oil. HPLC analysis of the product indicated that the starting material, (R)-7-carbomethoxy caprolactam was completely racemized and hydrolyzed to a 50/50 mixture of the R and S isomers of the corresponding racemic acids, (R)-7-carboxy caprolactam and (S)-7-carboxy caprolactam.

It is understood to those skilled in the art that if one would start with the (S)-7-carbomethoxy caprolactam as the starting material, the same racemic product mixture would result.

We claim:

1. A method of separating enantiomeric lactam esters comprising contacting the lactam esters with a biocatalyst in an aqueous solution, an organic solvents, or a mixture of organic and aqueous solvents wherein only one enantiomer is selectively hydrolyzed to give the optically active isomer of the corresponding acid, and separating the hydrolysis product from the unreacted lactam esters, wherein the lactams are of Formula II:

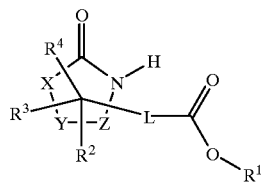

(II)

R¹ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

L is selected from the group consisting of no group or alkylene, alkenylene, and alkynylene;

wherein L may optionally be substituted by one or more of the following: alkyl, alkenyl, alkynyl, hydroxy, alkoxy, thiol, thioalkoxy, halogen, nitro, amino, alkylamino, dialkylamino, aminoalkyl, dialkylaminoalkyl, arylamino, aminoaryl, alkylaminoaryl, cyano, and haloalkyl;

X is selected from the group consisting of $(CH_2)_p$, and CH=CH;

p=1 to 4;

Y is selected from the group consisting of NH, O, $(CH_2)_q$ and CH=CH;

q=1 to 2;

Z is selected from the group consisting of $(CH_2)_v$ and CH=CH;

v=2;

$R^2$, $R^3$, and $R^4$ are independently selected from hydrogen, alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

2. A method of separating enantiomeric lactam esters comprising contacting the lactam esters with a biocatalyst in an aqueous solution, an organic solvents, or a mixture of organic and aqueous solvents wherein only one enantiomer is selectively hydrolyzed to give the optically active isomer of the corresponding acid, and separating the hydrolysis product from the unreacted lactam esters, wherein the lactams are of Formula III:

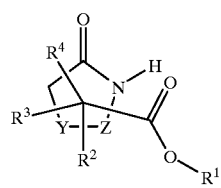

(III)

R¹ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen;

Y is selected from the group consisting of NH, O, $(CH_2)_q$ and CH=CH;

q=1 to 2;

Z is selected from the group consisting of $(CH_2)_v$ and CH=CH;

v=2;

$R^2$, $R^3$, and $R^4$ are independently selected from hydrogen, alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

3. A method of separating enantiomeric lactam esters comprising contacting the lactam esters with a biocatalyst in an aqueous solution, an organic solvent, or a mixture of organic and aqueous solvents wherein only one enantiomer is selectively hydrolyzed to give the optically active isomer of the corresponding acid, and separating the hydrolysis product from the unreacted lactam esters, wherein the lactam esters are of Formula V:

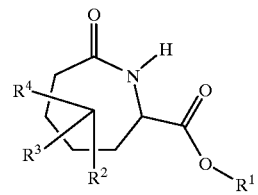

(V)

R¹ is selected from the group consisting of alkyl, alkenyl, alkynyl, cycloalkyl, cycloalkenyl, which may optionally be substituted by one or more of the following: alkyl, alkenyl, alkynyl, hydroxy, alkoxy, thiol, thioalkoxy, and halogen; and $R^2$, $R^3$, and $R^4$ are independently selected from hydrogen, alkyl, alkenyl, alkynyl, hydroxy, alkoxy, thiol, thioalkoxy, halogen, nitro, amino, alkylamino, dialkylamino, aminoalkyl, dialkylaminoalkyl, cyano, and haloalkyl, wherein all said substitutions may be optionally substituted with one or more of the following: halogen, alkyl, amino, alkylamino, dialkylamino, aminoalkyl, hydroxy, and alkoxy.

4. The method of claims 1, 2 or 3 wherein the biocatalyst is an enzyme or a microorganism.

5. The method of claims 1, 2 or 3 wherein the biocatalyst is an enzyme.

6. The method of claims 1, 2 or 3 wherein the biocatalyst is in an aqueous buffer solution.

7. The method of claims 1, 2 or 3 wherein the lactam esters are racemic.

8. The method of claims 1, 2 or 3 wherein the enzyme is a thermostable enzyme.

9. The method of claims 1, 2 or 3 wherein the reaction temperatures for the enzymatic resolution is in the range from 0° C. to 50° C.

10. The method of claims 1, 2 or 3 further comprising the step of racemizing one enantiomer of the lactam under basic conditions, and recycling the racemized lactam.

11. The method of claims 1, 2 or 3 further recovering the enzyme by precipitation with a salt and recycling the enzyme for reuse.

* * * * *